United States Patent [19]

Castaldi et al.

[11] Patent Number: 4,537,979

[45] Date of Patent: Aug. 27, 1985

[54] ALPHA-SUBSTITUTED-ALKYLARYLKETALS PARTICULARLY USEFUL FOR PREPARING ALPHA-ARYLALKANOIC ACIDS

[75] Inventors: Graziano Castaldi, Briona; Claudio Giordano, Vicenza, both of Italy

[73] Assignee: Zambon S.p.A., Vicenza, Italy

[21] Appl. No.: 520,130

[22] Filed: Aug. 3, 1983

[30] Foreign Application Priority Data

Mar. 7, 1983 [IT] Italy ............................. 19930 A/83

[51] Int. Cl.³ ............................................. C07D 321/00
[52] U.S. Cl. ....................................................... 549/347
[58] Field of Search ........................................... 549/347

[56] References Cited

U.S. PATENT DOCUMENTS 2,260,261 10/1941 Morey ................................. 549/347
3,116,298 12/1963 Sterling et al. ..................... 549/347
3,116,299 12/1963 Sterling et al. ..................... 549/347
3,658,846 4/1972 Chamberlin et al. ............... 549/347

FOREIGN PATENT DOCUMENTS 154575 9/1983 Japan ................................. 549/347

Primary Examiner—Ethel G. Love
Attorney, Agent, or Firm—Cushman, Darby & Cushman

[57] ABSTRACT

Alpha substituted alkylarylketals of formula:

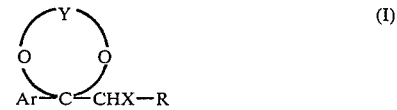

wherein
Ar is an aromatic radical having from 3 to 20 C atoms,
X is halogen, $OR_3$ (wherein $R_3$ is H, acyl or aroyl), $OSO_2CH_3$ or $OSO_2C_6H_4$—$CH_3$,
R is H or alkyl having from 1 to 3 C atoms,
Y is —$CH_2$—$C(R_1)$=$C(R_2)$—$CH_2$—(wherein, in turn, $R_1$ and $R_2$ are H or methyl).
The products of formula I are useful for preparing alpha-aryl-alkanoic acids.

2 Claims, No Drawings

ALPHA-SUBSTITUTED-ALKYLARYLKETALS PARTICULARLY USEFUL FOR PREPARING ALPHA-ARYLALKANOIC ACIDS

This invention relates to new alpha substituted alkylarylketals particularly useful for the preparation of alpha-arylalkanoic acids.

More particularly the new compounds according to this invention have the following formula:

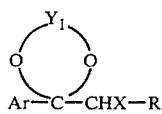
(I)

wherein
Ar is an aromatic radical having from 3 to 20 C atoms,
X is halogen, $OR_3$ (wherein $R_3$ is H, acyl or aroyl), $OSO_2CH_3$ or $OSO_2C_6H_4$—$CH_3$,
R is H or alkyl having from 1 to 3 C atoms,
Y is —$CH_2$—$C(R_1)$=$C(R_2)$—$CH_2$ (wherein, in turn, $R_1$ and $R_2$ are H or methyl).

The European Patent application Nos. 34.871 and 48.136 disclose cyclic ketals where X is, respectively, halogen, —O—$SO_2$—$CH_3$ or —O—$SO_2$—$C_6H_4$—$CH_3$, but they do not exemplify any ketal wherein Y is an unsaturated chain and form a ring having seven members.

Now it has been found that the ketals (I) show a higher activity and selectively in rearranging to esters because the presence of the double bond confers a higher reactivity and the seven member ring does not give those by-products which are formed as a consequence of the ring expansion when the ketals consisting in a ring having a lower number of members undergo rearrangement.

The ketals (I) may be prepared according to usual techniques such as the treatment of a ketone of formula (II)

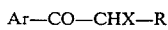

Ar—CO—CHX—R wherein X is halogen, Ar and R have the above mentioned meanings, with a diol of formula

HO—$CH_2$—$C(R_1)$=$C(R_2)$—$CH_2OH$ (III)

in the presence of a suitable catalyst.

Examples of methods suitable for preparing the ketals (I) where X is halogen contemplate the use of an acid catalyst as p-toluenesulfonic acid (*J. Org. Chem.* 21, 1366 (1956); ibidem, 22, 662 (1957); *Synthesis* 23, (1974), active montmorillonite (*Bull. Soc. Chim. France*, 2558, (1975), $BF_3$ etherate (*Bull. Soc. Chim. France*, 1763 (1975)) and citric acid (U.S. Pat. No. 3,936,398). An improvement to the last method contemplates the use of citric acid in the presence of hydroquinone which acts as polymerization inhibitor (*Bull. Soc. Chim. France*, 1973 (1975)).

The water generated in the course of the reaction is removed by azeotropic distillation with suitable solvents such as benzene, toluene, cyclohexane and the like or by means of dehydrating agents such as anhydrous $CuSO_4$, a trialkylorthoformate, molecular sieves and the like (Synthesis, 501 (1981)).

Other known methods for preparing the ketals are the trans-ketalization, the reaction of a ketone with a diol in the presence of a ketal such as 2,2-dimethoxypropane and an acid catalyst (*J. Org. Chem.* 25, 521, (1960)) and the reaction of a diol with a suitable enol-ether in the presence of an acid catalyst (*Bull. Soc. Chem. France*, 264 (1979)).

A preferred method for preparing the ketals (I) where X is OH comprises the reaction of a ketone (II) with an alcoholate of a diol (III); an excess of the diol (III) may be used as solvent. The alcoholate may be generated in situ by reacting the diol (III) with an alkali metal or a derivative thereof such as an hydride and an alkyl-derivative for example butyl-lithium. The thus obtained alpha-hydroxy-alkylarylketal may be then reacted with a mesyl or a tosyl halide to afford a ketal (I) wherein X is $OSO_2CH_3$ or $OSO_2$—$C_6H_4$—$CH_3$.

The ketals (I) are easily rearranged to form the esters of formula

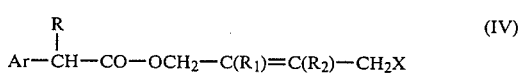
(IV)

wherein Ar, R, $R_1$, $R_2$ and X have the above mentioned meanings.

The rearrangement may be carried out according to known methods (European Patent application Nos. 34.871 and 48.136). A particularly preferred method for rearranging the ketals (I) where X is halogen, is described in the Italian Patent application No. 22.760 A/82, filed on Aug. 6, 1982 and comprises (a) the reaction of a ketal (I) in neutral or weakly alkaline conditions and in the presence of a polar protic medium and (b) the subsequent hydrolysis of the thus obtained ester (IV) in the same reaction medium to afford the corresponding alpha-arylalkanoic acid of formula

(V)

wherein Ar and R have the above mentioned meanings.

The ester (IV) are new and are a further object of this invention.

Examples of acid (V) useful as pharmaceutical owing to their anti-inflammatory, analgesic and antipyretic activity include aclofenac, benoxaprofen, caroprofen, dichlofenac, fenclofenac, fenoprofen, fentiazac, flurbiprofen, indoprofen, ibuprofen, isoprofen, ketoprofen, naproxen, piroprofen, suprofen, tolmetin, xenbucin and the like.

Examples of preferred products of formula (I), (II), (IV) and (V) include the following meanings
Ar is an aromatic ring selected from the group comprising (a) a phenyl ring substituted by one or two substituents selected from the group comprising halogen, 1-6 C alkyl, 1-4 C alkoxy, 2-4 C alkenyloxy, phenyl, phenoxy, dichlorophenoxy, dichloroanilino, benzoyl, indolinyl, dihydropyrrolyl, thenoyl (b) a naphthyl ring substituted by one or two substituents selected from the group comprising halogen and 1-4 C alkoxy (C) a pyrolyl ring substituted by one or two radicals selected from the group comprising 1-4 C alkyl and alkyl 1-4 C-phenyl, (d) chlorocarbazolyl, (e) benzoxazolyl substituted by one chlorophenyl radical, (f) thiazolyl substituted by one or two radical, selected from the group comprising phenyl and chlorophenyl, and (g) thienyl,
R is H or methyl, X is bromine, chlorine, OH, OSO$_2$CH$_3$ or, OSO$_2$C$_6$H$_4$—CH$_3$ Y is —CH$_2$—C(R$_1$)=C(R$_2$)—CH$_2$— (where R$_1$ and R$_2$ are hydrogen or methyl).

The following examples are given to illustrate this invention without limiting it in any way.

EXAMPLE 1

2-(4'-methoxyphenyl)-2-bromoethyl-4,7-dihydro-1,3-dioxepine 1-(4'-methoxyphenyl)-2-bromo-1-ethanone (*J. Org. Chem. Soc.* 68, 868 (1946)) (6.90 g; 30 mmols), cis-2-butene-1,4-diol (90 ml), citric acid (0.60 g; 2.9 mmols) and hydroquinone (0.30 g; 2.7 mmols) are reacted at 70° C. for 12 hours under reduced pressure (0.15 mm Hg) by distillating off slowly 120 ml of liquid which is replaced, time by time, with cis-2-butene-1,4-diol (120 ml). The reaction mixture is cooled and sodium methoxide (0.20 g) is added. The reaction mixture is poured into a 10% aqueous solution of sodium bicarbonate (300 ml) and extracted with ethyl ether (3×90 ml).

The combined ethereal extracts are washed with water (4×75 ml), dried over anhydrous sodium carbonate and evaporated in vacuo.

The residue (4.80 g) is chromatographed on a silica gel column (70–230 mesh; eluent, hexane/ethyl ether 9:1). There is thus obtained the title product (4.25 g; m.p. 59°–60° C., from methanol). $^1$H NMR (200 MHz) (CDCl$_3$ - TMS) delta (ppm): 3.70 (s, 2H); 3.82 (s, 3H); 4.26 (ABq, =28 4H, J=15 Hz); 5.68 (t, 2H, J=1, 65 Hz); 6.87–7.54 (AA'BB', 4H).

$^{13}$C NMR (CDCl$_3$ - TMS) delta (ppm): 36.09; 55.22; 62.80; 102.93; 113.21; 128.37, 129.48, 129.13, 159.65 (Ar).

I.R. =C=O stretching absent.

Water (150 ml) is added to the distilled liquid (120 ml) and the solution is extracted with chloroform (2×60 ml). The combined extracts are washed with water, dried over sodium sulfate and evaporated under vacuum to afford a residue consisting of non-reacted 1-(4'-methoxyphenyl)-2-bromo-1-ethanone (3.50 g; conversion, 65%). Yield of title product with respect to the reacted bromo-ketone, 85%.

Analogously the following products have been prepared:

2-(1'-bromoethyl)-2-(4'-isobutylphenyl)-4,7-dihydro-1,3-dioxepine $^1$H NMR (60 MHz) (CDCl$_3$ - TMS) delta (ppm): 0.91 (d, 6H, J=6 Hz); 1.52 (d, 3H, J=7 Hz); 1.96 (m, 1H); 2.50 (d, 2H, J=6 Hz); 4.24 (m, 4H); 4.60 (q, 1H, J=7 Hz); 5.56 (t, 2H, J=1,65 Hz); 6.95–7.50 (AA'BB', 4H).
I.R. =C=O stretching absent.

2-(1'-bromoethyl)-2-(4'-methoxyphenyl)-4,7-dihydro-1,3-dioxepine $^1$H NMR (60 MHz) (CDCl$_3$ - TMS) delta (ppm); 1.53 (d, 3H, J=7 Hz), 3.83 (s, 3H); 4.26 (m, J=1,66 Hz); 4.70 (q, 1H, J=7 Hz); 5.73 (t, 2H, J≈1.5 Hz); 6.68–7.73 (AA'BB', 4H).
I.R. =C=O stretching absent.

2-(1'-bromoethyl)-2-(6'-methoxy-2'-naphthyl)-4,7-dihydro-1,3-dioxepine m.p. 111°–113° C. (from methanol).

$^1$NMR (200 MHz) (CDCl$_3$ - TMS) delta (ppm), 1.56 (d, 3H, J=7 Hz); 3.93 (s, 3H); 4.30 (m, 4H); 4.70 (q, 1H, J=7 Hz); 5.66 (m, 2H); 7.12–8.00 (m, 6H).

$^{13}$C NMR (CDCl$_3$ - TMS) delta (ppm); 21.65 (CH$_3$); 50.77 (CH-Br); 55.35 (CH$_3$—O—); 63.08, 63.33 (—CH$_2$—); 105.01 (—O—C—O—); 105.51 (—CH=); 118.86, 125.72, 126.65, 128.27, 128.86, 129.36, 130.10 131.65, 134.49, 158.18 (Arom.)
I.R. =C=O stretching absent.

EXAMPLE 2

2-(6'-methoxy-2'-naphthyl)-2-(1'-hydroxyethyl)-4,7-dihydro-1,3-dioxepine

Metal sodium (0.23 g; 10 mmols) is added, at room temperature and under nitrogen atmosphere, to cis-2-butene-1,4-diol (15 ml) and the mixture is stirred until sodium is completely dissolved.

To the thus obtained solution, 2-bromo-1-(6'-methoxy-2'-naphthyl)- propan-1-one (*Bull. Soc. Chim. France,* 1962, 90) (1.46 g; 5 mmols) is added.

The reaction mixture is maintained under stirring for 4 hours at room temperature, then is poured into a 10% aqueous solution of sodium bicarbonate and extracted with ethyl ether (2×50 ml).

The combined ethereal extracts are washed with water to neutral, dried over anhydrous sodium sulfate and evaporated under vacuum.

The residue (1.56 g) is chromatographed on a silica gel column (70–230 mesh; eluent, ethyl ether) to afford the title product (0.40 g; yield, 26%), m.p. 96°–98° C. (from ethanol).

$^1$NMR (200 MHz) CDCl$_3$ - TMS delta (ppm); 1.50 (d, 3H, J=7 Hz); 2.64 (s, 1H); 3.93 (s, 3H); 4.30 (m, 5H); 5.69 (broad peak, 2H); 7.12–7.97 (m, 6H).
I.R. C=O stretching absent; 0—H stretching absent.

Analogously it has been prepared the 2-(4'-isobutylphenyl)-2-(1'-hydroxyethyl)-4,7-dihydro-1,3-dioxepine $^1$H-NMR (60 MHz) (CDCl$_3$ - TMS) delta (ppm); 0.95 (m, 2H); 1,85 (m, 1H); 2.5 (d, 2H, J=7 Hz); 4.3 (m, 5H); 5.7 (broad peak, 2H); 7.0–7.6 (m, 4H).
I.R. =C=O stretching absent.

EXAMPLE 3

2-(6'-methoxy-2'-naphthyl)-2-[1''-methylphenyl)-sulfonyloxyethyl]-4,7-dihydro-1,3-dioxepine p-toluensulfonyl chloride (1.26 g; 6.6 mmols) is added at room temperature and under nitrogen atmosphere to a solution of 2-(6'-methoxy-2'-naphthyl)-2-(1'-hydroxyethyl)-4,7-dihydro-1,3-dioxepine (1.80 g, 6 mmols) in pyridine (5 ml).

The reaction mixture is heated to 50° C. for 4 hours, then cooled, poured into water (50 ml) and extracted with ethyl ether (3×25 ml.

The combined ethereal extracts are washed with water to neutral, dried over anhydrous sodium sulfate and evaporated under nitrogen to afford a crude product (2;20 g; yield, 81%).

A sample analytically pure is obtained by chromatography on silica gel column (70–230 mesh; eluent, ethyl ether) and subsequent crystallization from ethanol. m.p. 124°–126° C.

Analogously the following products have been prepared:

2-(4'-isobutylphenyl)-2-[1'-(4''-methylphenyl)-sulfonyloxyethyl]-4,7-dihydro-1,3-dioxepine ¹H-NMR (60 MHz) (CDCl₃ - TMS) delta (ppm): 0.90 (d, 6H, J=7 Hz); 1.5 (d, 3H, J=7 Hz); 1.80 (m, 1H); 2.43 (s, 3H); 4.20 (m, 4H); 5.10 (q, 1H, J=7 Hz), 5.60 (broad peak, 2H); 7.1–8.0 (m, 8H).

I.R.—OH stretching absent.

2-(6'-methoxy-2'-naphthyl)-2-(1'-methylsulfonyloxyethyl)-4,7-dihydro-1,3-dioxepine ¹H-NMR (60 MHz) (CDCl₃ - TMS) delta (ppm): 1.30 (d, 3H, J=7 Hz); 3.15 (s, 3H); 3.95 (s, 3H); 4.35 (m, 4H); 5.25 (q, 1H, J=7 Hz); 5.7 (broad peak, 2H); 7.1–8.1 (m, 6H).

I.R.—OH stretching absent

2-(4'-isobutylphenyl)-2-(1'-methylsulfonyloxyethyl)-4,7-dihydro-1,3-dioxepine ¹H-NMR (60 MHz) (CDCl₃ - TMS) delta (ppm): 0.9 (d, 6H, J=7 Hz); 1.25 (d, 3H, J=7 Hz); 1.8 (m, 1H); 2.5 (d, 2H, J=7 Hz); 3.1 (s, 3H); 4.3 (m, 4H); 5.15 (q, 1H J=7 Hz); 5.7 (broad peak, 2H); 7.1–7.6 (AA'BB', 4H).

I.R.—OH stretching absent.

EXAMPLE 4

A mixture of 2-(6'-methoxy-2'-naphthyl)-2-(1'-methylsulfonyloxyethyl)-4,7-dihydro-1,3-dioxepine (1.13 g; 3 mmol) ethylene glycol (10 ml) and potassium acetate (0.50 g; 5 mmol) is heated to 130° C. for 1.5 hours. The reaction mixture is then poured into water (50 ml) and extracted with ethyl ether (3×35 ml). the combined ethereal extracts are washed with water and dried over sodium sulfate. By evaporation of the solvent under vacuum there is obtained a residue which is dissolved in a 30% solution of NaOH (5 ml) in methanol (15 ml). The reaction mixture is refluxed for 12 hours and then diluted with water and extracted with ethyl ether (3×35 ml). The extracts are washed with water to neutral, dried over sodium sulfate and evaporated under vacuum to afford a solid residue consisting of 2-(6'-methoxy-2'-naphthyl)-propionic acid (0.57 g; yield, 82%) m.p. 154°–156° C.

We claim:

1. A compound of formula

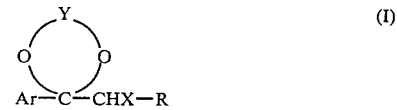

wherein

Ar is a phenyl ring substituted by one or two substituents selected from halogen, 1–6 C alkyl, 1–4 C alkoxy, 2–4 C alkenyloxy or a naphthyl ring substituted by one or two substituents selected from halogen and 1–4 C alkoxy;

X is $OR_3$ in which $R_3$ is H, acyl or aroyl, $OSO_2$—$CH_3$ or $OSO_2$—$C_6H_4$—$CH_3$;

R is H or an alkyl having from 1 to 3 C atoms;

and Y is —$CH_2$—$C(R_1)$=$C(R_2)$—$CH_2$— in which $R_1$ and $R_2$ are H or $CH_3$.

2. A compound of formula

wherein

Ar is a phenyl ring substituted by one or two substituents selected from halogen, 1–6 C alkyl, 1–4 C alkoxy, 2–4 C alkenyloxy, phenyl, phenoxy, dichlorophenoxy, dichloroanilino, benzoyl, or a naphthyl ring substituted by one or two substituents selected from halogen and 1–4 C alkoxy;

X is $OR_3$ in which $R_3$ is H, acyl or aroyl, $OSO_2$—$CH_3$ or $OSO_2$—$C_6H_4$—$CH_3$;

R is H or an alkyl having from 1 to 3 C atoms;

and Y is —$CH_2$—$C(R_1)$=$C(R_2)$—$CH_2$— in which $R_1$ and $R_2$ are H or $CH_3$.

* * * * *